United States Patent [19]

Belli Dell'Amico et al.

[11] Patent Number: 5,075,260

[45] Date of Patent: Dec. 24, 1991

[54] SILICON AND ALUMINUM N,N-DIALKYLCARBAMATES AND THEIR HYDROLYSIS PRODUCTS AND PROCESS FOR THEIR PREPARATION

[75] Inventors: Daniela Belli Dell'Amico, Pisa; Fausto Calderazzo, Ghezzano; Michela Dell'Innocenti, Calci, all of Italy

[73] Assignee: Consiglio Nazionale Delle Ricerche, Rome, Italy

[21] Appl. No.: 500,997

[22] Filed: Mar. 29, 1990

[30] Foreign Application Priority Data

Apr. 27, 1989 [IT] Italy ................ 20284 A/89

[51] Int. Cl.⁵ ........................... C07F 7/10
[52] U.S. Cl. ..................... 556/420; 556/183
[58] Field of Search ................. 556/420, 183

[56] References Cited

U.S. PATENT DOCUMENTS

| | | | |
|---|---|---|---|
| 2,052,138 | 8/1936 | Hopff et al. | 556/183 |
| 3,056,820 | 10/1962 | Martinek | 556/183 X |
| 3,284,485 | 11/1966 | Goossens | 556/420 X |
| 4,400,526 | 8/1983 | Kanner et al. | 556/420 |
| 4,631,346 | 12/1986 | Webb et al. | 556/420 |
| 4,831,173 | 5/1989 | Knausz et al. | 556/420 |
| 4,837,349 | 6/1989 | Ohfune et al. | 556/420 |

*Primary Examiner*—Paul F. Shaver
*Attorney, Agent, or Firm*—Birch, Stewart, Kolasch & Birch

[57] ABSTRACT

Silicon and aluminium N,N-dialkylcarbamates are prepared by reacting a secondary amine and $CO_2$ with respectively a silicon and an aluminium halide in a reaction medium consisting of an organic solvent. The respective hydrolysis products are obtained from said N,N-dialkylcarbamates by treatment with water in tetrahydrofuran.

2 Claims, No Drawings

SILICON AND ALUMINUM N,N-DIALKYLCARBAMATES AND THEIR HYDROLYSIS PRODUCTS AND PROCESS FOR THEIR PREPARATION

FIELD OF THE INVENTION

The present invention relates to silicon and aluminium organic derivatives and a process for their preparation.

SUMMARY OF THE INVENTION

This invention relates to new organic silicon and aluminium compounds, namely N,N-dialkylcarbamates of general formula (I):

$$M[O_2CNR_2]_n \qquad (I)$$

where M is Si or Al, n is 4 when M is Si and 3 when M is Al, and R is a $C_1-C_6$ alkyl group.

The invention also relates to the hydrolysis products of the compounds (I) and to the process for preparing the compounds (I) and their hydrolysis products.

The process for preparing the compounds (I) and their hydrolysis is characterized by:

a) reacting a secondary amine and $CO_2$ with an $MX_n$ halide in which M is Si or Al, X is Cl or Br, and n is 4 when M is Si and 3 when M is Al, in a reaction medium consisting of an organic solvent;

b) filtering off the dialkyammonium chloride which forms;

c) precipitating the compound (I) by concentrating the filtered solution, and if necessary cooling and adding n-heptane;

d) recovering the product (I) by filtration;

e) dissolving the product (I) in tetrahydrofuran and hydrolyzing with water;

f) recovering the hydrolysis product by filtration.

DETAILED DESCRIPTION OF THE INVENTION

The characteristics and advantages of the silicon and aluminium N,N-dialkyl-carbamates of formula (I) and their hydrolysis products, and the process for preparing the compounds (I) and their hydrolysis products will be more apparent from the following detailed description.

The compounds of formula (I) are prepared by reacting a secondary amine and $CO_2$ with a $MX_n$ halide as heretofore defined. To effect this reaction, a solution of $MX_n$ in an organic solvent is gradually added to a solution of $R_2NH$ and $CO_2$ in an organic solvent. The organic solvent is chosen from the group comprising saturated aliphatic and aromatic hydrocarbons and is preferably toluene. The organic solvent has a water content of less than 50 ppm.

The concentration of the secondary amine solution is between 0.5 and 5 moles/l and the concentration of the $MX_n$ solution is between 0.1 and 2 moles/l.

The molar ratio of secondary amine to $MX_n$ used in the reaction is between 8 and 12.

The $MX_n$ solution is added to the secondary amine solution under a $CO_2$ atmosphere.

When the addition is complete the reaction mixture is kept stirring at a temperature of between 15° C. and 30° C. under a $CO_2$ atmosphere for a time of between 4 and 8 hours.

On termination of the reaction the mixture consists of a colorless solution of (I) and a colorless solid consisting of dialkylammonium chloride.

The reaction mixture is filtered and the solution recovered. To recover (I) when M is Si, the solution is concentrated by evaporating the solvent at ambient temperature under reduced pressure, until a concentration of (I) of between 1 and 2 moles/l is obtained, then cooling to −30° C. and adding n-heptane in a quantity of between 1 and 3 volumes per volume of solution while maintaining the temperature at −30° C.

The product (I) in which M is Si thus precipitates, and is separated by filtration under a $CO_2$ atmosphere.

To recover (I) when M is Al, the solution is evaporated to dryness, under reduced pressure, the residue taken up in n-heptane and the product separated by filtration.

To hydrolyze the compound (I), it is dissolved in anhydrous tetrahydrofuran and then treated with $H_2O$.

The compound (I) is dissolved in the tetrahydrofuran under an atmosphere of dry argon, the quantities used being such as to obtain a concentration of (I) in the tetrahydrofuran which ranges from 0.05 to 2 moles/l.

$H_2O$ is added to the solution in such a quantity so as to obtain a molar ratio of $H_2O$ to M of between 2 and 4.

This reaction is conducted at ambient temperature for 0.5–2 hours while keeping the mixture stirred.

The hydrolysis product is a colorless solid which is recovered by filtration.

The compounds (I) are soluble in both aromatic and aliphatic hydrocarbons, and are very sensitive to atmospheric moisture, by which they hydrolyze rapidly.

The hydrolysis products of the compounds (I) find important use in the production of very pure zeolites, with the introduction of the cations of interest.

The following examples of the preparation of the compounds according to the invention are given by way of non-limiting illustration.

EXAMPLE 1

$SiCl_4$ (5 ml; 0.043 moles) dissolved in anhydrous toluene (100 ml) is added slowly under a carbon dioxide atmosphere to a solution of 35.5 g (0.485 moles) of diethylamine $MHEt_2$ in anhydrous toluene (200 ml). After stirring for 5 hours at a temperature of 23° C. in a $CO_2$ atmosphere, the reaction mixture is comprised of a colorless solution and a colorless solid consisting of diethylammonium chloride. The reaction mixture was filtered under $CO_2$ and the solution was recovered, for which the chloride test was found negative, was concentrated under reduced pressure ($10^{-2}$ Torr) to a volume of 30 ml, and cooled to about −30° C.

This treatment resulted in the partial crystallization of the silicon N,N-diethylcarbamate, which was recovered as a colorless solid by filtration and dried at 20° C. under reduced pressure to obtain 5.7 g of product. After cooling the toluene solution, resulting from the filtration, to about −30° C. and adding 30 ml of n-heptane, a further 12.45 g of product were recovered, to give an overall yield of 86% on the silicon tetrachloride used.

The product was analyzed for silicon content by combustion and for carbon dioxide content by decomposing with 20% sulphuric acid and measuring the volume of the gas evolved. Analysis: % found (calculated values for $C_{20}H_{40}N_4O_8Si$ being given in parentheses): Si, 5.7 (5.7); $CO_2$, 32.9 (35.7). The compounds has an intense IR band at 1710 $cm^{-1}$ due to the coordinated carbamate grouping. The $^1H$-NMR spectrum shows two resonances corresponding to absorption of the methylene and methyl groups bonded to the nitrogen of the carbamate group. $Si[O_2CN(CH_2CH_3)_2]_4$

EXAMPLE 2

Example 1 is repeated, using diisopropylamine in place of the diethylamine.

Silicon N,N-diisopropylcarbamate, $Si[O_2CNPr_2]_4$, was obtained and was analyzed for its silicon and carbon dioxide content as indicated in Example 1. Analysis: % found (calculated values for $C_{28}H_{56}N_4O_8Si$, being given in parentheses): Si, 4.2 (4.6); $CO_2$, 26.8 (29.1). $CO_2$:Si molar ratio = 4.1.

EXAMPLE 3

The silicon N,N-diethylcarbamate, $Si[O_2CNEt_2]_4$, obtained in Example 1 (2.47 g; 5.01 mmoles) was dissolved in anhydrous tetrahydrofuran (100 ml) under a dry argon atmosphere and treated with 0.36 g (20.0 mmoles) of $H_2O$ at ambient temperature. A colorless suspension immediately formed and was kept stirring for 1 hour after which it was filtered under argon. The resultant finely divided colorless solid was dried for 12 hours under reduced pressure (about $10^{-2}$ Torr) at ambient temperature. 0.401 g were obtained with a yield of 90.3% based on the silicon content of the product. Analysis: % found (calculated values for $[NH_2(C_2H_5)_2]_2Si_8O_{17}\cdot 3H_2O$, $C_8H_{30}N_2O_{20}Si_8$ given in parentheses): C, 14.2; 12.9 (13.7); H, 3.8; 3.6 (4.3); N, 3.1; 3.3 (4.0); Si, 31.7 (32.1).

EXAMPLE 4

Example 3 was repeated using a $H_2O$:Si molar ratio of 2.

A finely divided colorless product was obtained, of appearance similar to the product of Example 3.

The product had the following analytical composition: C, 15.0%; H, 4.2%; N, 4.0%.

EXAMPLE 5

30 ml (21.66 g; 214 moles) of $NH(iC_3H_7)_2$ are dissolved in 200 ml of anhydrous toluene at atmospheric pressure under carbon dioxide. 5.05 g of $AlBr_3$ (18.9 mmoles) are then added and the resultant suspension is stirred at ambient temperature for 7 hours. After filtering off the di-isopropylammonium hydrobromide which forms, the carbamate solution is evaporated to dryness under reduced pressure. The residue is taken up in n-heptane (30 ml), the resultant suspension is filtered and the aluminium dialkylcarbamate which collects on the filter is dried under a mechanical pump (ca. $10^{-1}$ mmHg) for 2 hours. 4.3 g of product are obtained with a yield of 49.5%. The colorless microcrystalline product has good solubility in aromatic hydrocarbon solvents, moderate solubility in saturated hydrocarbon solvents and good solubility in $CCl_4$.

Elemental analysis: found % (calculated values for $Al[O_2CN(C_3H_7)_2]_3$, $C_{21}H_{42}AlN_3O_6$ given in parentheses): C, 53.0 (54.9); H, 8.9 (9.2); Al, 6.0 (5.9); $CO_2$, 27.3 (28.7); N, 8.4 (9.1). The product is very sensitive to atmospheric moisture. The infrared band (in polychlorotrifluoroethylene) shows absorption bands at 2960, 2930, 2880, 1620, 1550 f, 1500 f.

We claim:

1. A N,N-dialkylcarbamate of the general formula (I)

$$M[O_2CNR_2]_n \qquad (I)$$

wherein M is Si, n is 4 and R is a $C_1$-$C_6$ alkyl group.

2. A process for preparing a N,N-dialkylcarbamate of the general formula (I)

$$M[O_2CNR_2]_n \qquad (I)$$

wherein M is Si, n is 4 and R is a $C_1$-$C_6$ alkyl group which consists of:

a) reacting a secondary amine and $CO_2$ with $MX_n$ wherein M is Si, n is 4, and X is Cl or Br, in an organic solvent selected from the group consisting of a saturated aliphatic and an aromatic hydrocarbon having a water content of less than 50 ppm, at a temperature of from 15° C. to 30° C., in a $CO_2$ atmosphere, for a period of time of between 4 and 8 hours, said secondary amine and $MX_n$ being in a molar ratio of from 8 to 12;

b) filtering off dialkylammonium chloride which forms as a result of said reaction (a);

c) precipitating said compound (I) by concentrating a filtered solution collected in step (b) up to a concentration of between 1 and 2 moles/l, cooling to $-30°$ C. and adding n-heptane in a quantity of between 1 and 3 volumes of solution while maintaining the temperature at $-30°$ C.; and d) recovering said compound (I) by filtration.

* * * * *